United States Patent
Ranganathan

(10) Patent No.: US 7,026,160 B2
(45) Date of Patent: Apr. 11, 2006

(54) ORAL BACTERIOTHERAPY COMPOSITIONS AND METHODS

(75) Inventor: Nataragan Ranganathan, Broomall, PA (US)

(73) Assignee: Kibow Biotech, Inc., Philadelphia, PA (US)

(*) Notice: Subject to any disclaimer, the term of this patent is extended or adjusted under 35 U.S.C. 154(b) by 37 days.

(21) Appl. No.: 10/676,622

(22) Filed: Sep. 30, 2003

(65) Prior Publication Data

US 2004/0106185 A1    Jun. 3, 2004

Related U.S. Application Data

(63) Continuation-in-part of application No. 09/855,346, filed on May 15, 2001, now Pat. No. 6,706,287, which is a continuation-in-part of application No. 09/557,011, filed on Apr. 20, 2000, now Pat. No. 6,706,263.

(60) Provisional application No. 60/131,774, filed on Apr. 30, 1999.

(51) Int. Cl.
  *C12N 1/20*    (2006.01)
  *A61K 9/28*    (2006.01)
  *A61K 9/48*    (2006.01)

(52) U.S. Cl. ............... 435/252.5; 424/93.4; 424/93.46; 424/463; 424/474

(58) Field of Classification Search ............... 424/93.1, 424/93.4, 93.45, 93.46, 94.6, 463, 474; 435/252.5
See application file for complete search history.

(56) References Cited

U.S. PATENT DOCUMENTS

| | | | | |
|---|---|---|---|---|
| 6,025,152 | A | * | 2/2000 | Hiatt ............................. 435/42 |
| 6,080,401 | A | * | 6/2000 | Reddy et al. ............... 424/93.3 |
| 2002/0192202 | A1 | | 12/2002 | Naidu ...................... 424/93.45 |
| 2003/0147995 | A1 | | 8/2003 | Koss et al. .................... 426/72 |

OTHER PUBLICATIONS

Holzapfel et al., "Overview of gut flora and probiotics", International Journal of Food Microbiology 1998 41:85-101.

Marteau et al., "Protection from gastrointestinal diseases with the use of probiotics[1-3]", Am J. Clin Nutr 2001 73: 430S-436S.

Orrhage and Nord, "*Bifidobacteria* and *Lactobacilli* in Human Health", Drugs Exptl. Clin. Res. 2000 XXVI(3):95-111.

Pateras et al., "The Role of Intestinal Perfusion in the Management of Chroniic Uremia", Trans. Amer. Soc. Artif. Int. Organs 1964 X:292-295.

von Wright and Salminen, "Probiotics:established effects and open questions", Eur J Gastroenterol Hepatol 1999 11(11):1195-1198.

* cited by examiner

*Primary Examiner*—Ruth A. Davis
(74) *Attorney, Agent, or Firm*—Licata & Tyrrell P.C.

(57) ABSTRACT

A composition for treatment of renal failure with selected bacteria which converts nitrogenous waste into non-toxic compounds in vivo is provided. Also provided is a method of inhibiting build up of toxins and metabolic wastes and overgrowth of undesirable bacteria in a subject by administering the composition to the subject.

1 Claim, No Drawings

ORAL BACTERIOTHERAPY COMPOSITIONS AND METHODS

CROSS REFERENCE TO RELATED APPLICATIONS

This application is a continuation-in-part of U.S. patent application Ser. No. 09/855,346 filed May 15, 2001 now U.S. Pat. No. 6,706,287, which is a continuation-in-part of U.S. patent application Ser. No. 09/557,011 filed Apr. 20, 2000, now U.S. Pat. No. 6,706,263, which is a conversion of U.S. Provisional Application 60/131,774 filed Apr. 30, 1999.

INTRODUCTION

This work is partly funded from the Small Business Innovation Research (SBIR) grant award from the National Institutes of Diabetes, Digestive and Kidney (NIDDK) Diseases, National Institute of Health (NIH), Bethesda, Md. Grant No: 1R44DK61873-01.

1. Field of the Invention

The invention relates to compositions and methods of using these compositions in vivo to treat renal, hepatic and gastrointestinal diseases by eliminating toxins and other metabolic waste products and reducing or retarding undesirable bacterial over growth. In one embodiment, the composition of the present invention comprises a live selected bacteria instilled into the gastrointestinal tract of a subject. The selected bacteria is preferably *B. pasteurii* or *L. sporogenes*.

2. Background of the Invention

Kidney disease is ranked fourth among the major diseases in the United States afflicting over 20 million Americans. More than 90,000 patients die each year because of kidney diseases. In recent years the number of chronic kidney failure patients has increased about 11 percent annually. About 80,000 Americans on dialysis die of various complications each year and more than 27,000 are on waiting lists for kidney transplants each year with only about 11,000 of these patients receiving transplants. Further, nearly 350,000 Americans suffer from end stage renal disease (ESRD), which is the final stage in chronic renal failure.

In normal, healthy humans, metabolic waste nitrogen is primarily excreted via the kidneys as urea, uric acid creatinine, etc. in the urine. However, in individuals with kidney disease, as well as a number of other diseases such as inborn errors in urea cycle enzyme deficit, waste nitrogen accumulates in the body thereby manifesting toxic symptoms. Hyperammonium can lead to mental retardation and, in severe cases, coma.

Currently hemo- or peritoneal- dialysis and renal transplant are the only treatment modalities. However, the economic costs of these treatment modalities are extremely high. For example, in 1996 in the United States alone, the annual cost of ESRD treatment was over 14 billion dollars. In developing and underdeveloped countries with low health care budgets, ESRD patients are deprived access to such treatments due to their high costs. Accordingly, there is a need for alternative modalities of treatment for uremia.

A number of treatment attempts have been based on the use of the bowel as a substitute for kidney function. During a normal digestive process the gastrointestinal tract delivers nutrients and water to the bloodstream and eliminates some waste products and undigested materials through the bowel. The intestinal wall regulates absorption of nutrients, electrolytes, water and certain digestive aiding substances such as bile acids. The intestinal wall also acts as a semipermeable membrane allowing small molecules to pass from the intestinal tract into the bloodstream and preventing larger molecules from entering the circulation.

Nitrogenous wastes such as urea, uric acid, creatinine and uric acid, along with several other small and medium molecular weight compounds, flow into the small intestine and equilibrate across the small intestine epithelium. Studies of intestinal dialysis have shown a daily flow of 71 grams of urea, 2.9 grams of creatinine, 2.5 grams of uric acid and 2.0 grams of phosphate into the intestinal fluid (Sparks, R. E. Kidney Int. Suppl. 1975 Suppl 3, 7:373–376). Accordingly, various invasive and noninvasive attempts including external gut fistula, intestinal dialysis, induced diarrhea, and administration of oral sorbents and/or encapsulated urease enzyme have been made to extract uremic waste from the gastrointestinal tract (Twiss, E. E. and Kolff, W. J. JAMA 1951 146:1019–1022; Clark et al. Trans. Am. Soc. Artif. Intrn. Organs 1962 8:246–251; Pateras et al. Trans. Am. Soc. Artif. Intrn. Organs 1965 11:292–295; Shimizu et al. Chemical Abstracts 1955 103:129004; Kjellstrand et al. Trans. Am. Soc. Artif. Intern. Organs 198127:24–29; and Kolff, W. J. Kidney Int. 1976 10:S21114 S214).

In addition, genetically engineered *E. herbicola* cells have been encapsulated and demonstrated to convert ammonia into usable amino acids for the cells before being eliminated via the bowel. Microencapsulated genetically engineered *E. coli* DH5 cells have also been shown to be effective in removal of urea and ammonia in an in vitro system and in a uremic rat animal model (Prakash, S. and Chang, T. M. S. Biotechnology and Bioengineering 1995 46:621–26; and Prakash, S. and Chang, T. M. S. Nature Med. 19962: 883–887). However, administration of genetically engineered bacteria poses regulatory and safety concerns and raises ethical issues which may lead to noncompliance by patients.

The human gastrointestinal tract harbors a complex microbial ecosystem containing a large number and variety of bacteria. The resident bacterial population in the human gastrointestinal tract has a major impact on gastrointestinal function and thereby on human health and well being. Among these, some bacteria are opportunistic or considered to be detrimental and cause adverse conditions such as diarrhea, infections, gastroenteritis and endotoxaemia, while some bacteria species are considered as "probiotic", in that they perform beneficial functions for the human organism (Holzapfel W H, et al. *Int J Food Microbiol* 1998 May 26; 41(2): 85–101).

Among the probiotic bacteria, *Bifidobacteria* species are the most prominent. *Bifidobacteria* species, when in live and viable form, stimulate the immune system and exert a competitive exclusion of pathogenic and putrefactive bacteria, reduce the amounts of ammonia and cholesterol in the blood, and promote absorption of minerals. In addition, *Bifidobacteria* have been suggested to exert a preventive action against colon cancer, by reducing the activity of some enzymes that convert procarcinogen substances into carcinogen substances (von Wright, et al. *Eur J Gastroenterol Hepatol* 1999 November; 11(11): 1195–1198).

The lactic bacteria such as *Lactobacillus bulgaricus, Lactobacillus acidophilus, Lactobacillus casei, Lactobacillus plantarum* and *Streptococcus faecium. Streptococcus thermophilus* are also probiotic. These bacteria produce antagonist effects against pathogenic microorganisms, stimulate the immune system, improve lactose digestion, perform a lypolytic activity making fats more digestible, reduce plasmatic values of cholesterol, protect the intestinal mucosa ensuring an even assimilation of the nutritive substances, produce polysaccharides that are active on some tumors, and reduce viability of some enzyme-producing microorganisms catalyzing conversion of procarcinogen substances into carcinogenic substances.

It is believed that the probiotic bacteria exert their effects in a synergistic manner to curtail and retard the growth of pathogenic/detrimental bacteria of the gut (Marteau, P R et al. Am J Clin Nutr February; 73(2 Suppl): 430S–436S; Cummings J H, et al. Am J Clin Nutr 2001 February; 73(2 Suppl): 415S–420S).

The intestinal bacteria flora can be reduced, become unbalanced or be eliminated in patients undergoing antibiotic treatment and other therapies, and in individuals suffering from inflammatory intestinal diseases, kidney disease and liver disease. In addition, it has been shown that during normal aging the *Bifidobacteria* population is reduced while the concentration of pathogenic and putrefactive bacteria concomitantly increases (Orrhage K., et al. Drugs Exp Clin Res 2000; 26(3): 95–111).

It is also known that beneficial effects of microbes such as the *Bifidobacterium* species are in part due to their ability to ferment nondigestible sugars, known as prebiotics, present in the colon. A prebiotic is a non-digestible food ingredient that beneficially affects the host by selectively stimulating the growth and/or the activity of one or a limited number of bacteria in the colon. Prebiotics are typically thought of as carbohydrates of relatively short chain length. Prebiotics are like other carbohydrates that reach the cecum, such as nonstarch polysaccharides, sugar alcohols, and resistant starch, in being substrates for fermentation. They are, however, distinctive in their selective effect on the microflora. To be effective, prebiotics they must reach the cecum (Bezkorovainy, A. Am J Clin Nutr 2001 February; 73(2 Suppl): 399S–405S).

U.S. Pat. No. 5,733,568 teaches the use of microencapsulated *Lactobacillus* bacteria for treatment of antibiotic associated or other acute and chronic diarrhea as well as for skin and vaginal yeast infections. The microencapsulation is said to prevent inactivation of the bacillus and to deliver it to the intestine as well as to avoid lactose intolerance seen in said diarrheas.

U.S. Pat. No. 5,032,399 teaches the use of species of *Lactobacillus acidophilus* to adhere to intestinal mucosa and thereby reduce gastrointestinal side effects of antibiotic therapy that reduces beneficial bacteria population.

U.S. Pat. No. 5,531,988 teaches, in addition to beneficial bacteria, use of immunoglobulin in the composition as a dietary supplement.

U.S. Pat. No. 5,840,318 also teaches a beneficial bacterial composition that can modulate the immune system of animals.

Use of probiotics such as *Lactobacillus acidophilus* has been suggested to curtail the bacterial overgrowth and the accumulation of uremic toxins and carcinogenic compounds. Unabsorbable carbohydrate in the diet of uremic patients has also been shown to increase fecal nitrogen. Use of lactulose and dietary fiber has also been shown to reduce plasma urea 11 to 27% and increase fecal nitrogen excretion to 39 to 62% (Wrong, O., Nature Medicine 2–3, 1997).

SUMMARY OF THE INVENTION

An object of the present invention is to provide a composition for treatment of renal failure comprising a selected bacteria which converts nitrogenous waste into non-toxic compounds in vivo.

A further object of the present invention is to provide a method of inhibiting build up of toxins and metabolic wastes and overgrowth of undesirable bacteria in a subject comprising administering to a subject a composition comprising a selected bacteria which converts nitrogenous waste into non-toxic compounds in vivo.

DETAILED DESCRIPTION OF THE INVENTION

In kidney failure there is a decrease in the glomerular filtration rate and the kidneys are unable to maintain homeostasis of the blood. Homeostatic balance of water, sodium, potassium, calcium and other salts is no longer possible and nitrogenous wastes are not excreted. Retention of water causes edema and as the concentration of hydrogen ions increases, acidosis develops. Nitrogenous wastes accumulate and a condition referred to as uremia develops in the blood and tissue. Uremic toxins can be defined as solutes that: (I) are normally excreted by healthy kidneys, (ii) accumulate progressively during the development of renal failure so that their concentration increases, and (iii) inhibit various physiologic and biochemical functions; as a whole, they contribute to a complex set of clinical symptoms that comprise the Uremic Syndrome. Examples of uremic toxins include, but are not limited to, ammonia, urea, creatinine, phenols, indoles, and middle molecular weight molecules. More specifically, in uremia, the concentration of serum creatinine, blood urea nitrogen (BUN), uric acid, and guanidino compounds such as N-methyl guanidine (NMG) and guanidino succinic acid, (GSA) are significantly altered with accompanying abnormalities in acid-base equilibrium, electrolytes and water retention. In addition there are several known and unknown substances of low and middle molecular weight which have been identified as uremic toxins which also accumulate. If untreated the acidosis and uremia can cause coma and eventually death.

The introduction of renal dialysis has contributed to rapid progress in the clinical treatment of renal failure and elucidation of uremia. When a patient has mild kidney failure where the serum creatinine level is less than 400 μmol/L, the patient does not require renal replacement therapy such as dialysis or renal transplant. However, in general, when the serum creatinine level rises to 900 μmol/L, the patient needs routine dialysis or a kidney transplant to survive.

Dialysis can serve as a lifetime therapy for ESRD patients. Phosphate binders such as calcium acetate, calcium carbonate or aluminum hydroxide are generally prescribed for uremic patients receiving dialysis to reduce elevated phosphate levels. In general, however, dialysis is very expensive, inconvenient, time consuming and may occasionally produce one or more side effects. With a successful kidney transplant, a patient can live a more normal life with less long-term expense. However, there are also high costs associated with transplant surgery, the recovery period and the continuous need for anti-rejection medications. Further, there are often times a shortage of suitable donors. Accordingly there is a need for alternative strategies.

The present invention provides a composition comprising one or more selected bacteria which when instilled into the gastrointestinal tract of a subject converts nitrogenous wastes accumulated in the subject due to renal insufficiency into nontoxic compounds. The term subject is meant to include humans. In renal patients, nitrogenous solutes traverse intestinal capillaries into the bowel through diffusion. The composition of the present invention can be administered orally, or through any other appropriate manner so that the selected bacteria are instilled into the gastrointestinal tract of the subject and nitrogenous wastes are reduced.

The selected bacteria are live bacteria which consume excess urea, creatine, and "uremic" solutes. The selected bacteria are preferably *Bacillus pasteurii* or *Lactobacillus sporogenes*.

The present invention further provides an in vivo method of reducing nitrogenous wastes due to renal failure in a subject comprising instilling selected bacteria into the gastrointestinal tract of the subject so that nitrogenous wastes are converted into nontoxic compounds by the selected bacteria. The selected bacteria of the compositions of the present invention may be instilled via any suitable means including but not limited oral administration of the selected bacteria as a pharmaceutical composition or food stuff, injection, surgical implantation, or intranasal administration. It is preferred that the compositions of the present invention be administered to the animal on a routine basis such as one or more times daily over a period of time. Reduction of nitrogenous wastes is indicated via blood, urine or fecal sample testing wherein a reduction in BUN levels or serum creatine levels of the blood, urine or fecal samples as compared to initial or control levels indicates effective treatment. The compositions of the present invention are useful for treatment of renal failure.

The present invention further provides a method of inhibiting build up of toxins and metabolic wastes and overgrowth of undesirable bacteria in a subject comprising administering to a subject a composition comprising one or more selected bacteria which when instilled into the gastrointestinal tract of a subject converts nitrogenous wastes accumulated in the subject into nontoxic compounds. The composition can be administered to the subject to alleviate the symptoms of uremia caused by kidney disease or an inborn error of urea metabolism. The compositions of the present invention may be administered to treat renal insufficiency, liver insufficiency, inborn error of urea metabolism or gastrointestinal disorders and diseases.

For example, Sprague-Daly rats weighing 281.20=/−41.6 gm were subjected to ⅚th nephrectomy after measurement of baseline weight, BUN, serum creatinine, urine volume and fecal flora composition. The study group consisted of 36 nephrectomized rats and 6 controls. After a two-week post surgery stabilization, cohorts of six rats were fed standard rat chow plus one of the following regimens: 1) placebo, 2) *B. pasteurii* 3) *L. sporogenes*, 4) *L. acidophilus, L. bulgaricus; Bifidus, S. thermophiles, L. casei,* and *L. reuteri*, 5) *L. acidophilus, L. bulgaricus, Bifidus, S. thermophilus* and 6) *S. boulardii*. Subsequent blood, urine, and fecal measurements were obtained every 30 days for a total of 120 days.

The subtotally nephrectomized rats fed *B. pasteurii* and *L. sporogenes* had lower BUN levels (62.0+/−21, 63.0+/−26 mg/dl) compared with placebo (99.0+/−46 mg/dl) a reduction of (38 and 37%). Serum creatine levels were similarly reduced in rats fed with *B. pasteurii* and *L. sporogenes* (0.9+/−)0.25, 0.9+/−0.2 mg/dl) compared to placebo (1.5+/−0.56 mg/dl) a reduction of 40% in both groups. Rats fed with regimens comprising only *L. acidophilus, L. bulgaricus; Bifidus, S. thermophiles, L. casei, L. reuteri, L. acidophilus, L. bulgaricus, Bifidus, S. thermophilus* or *S. boulardii* did not show significant difference in BUN or serum creatine, compared to placebo. Feeding increased the fecal count for the appropriate group of bacteria in all groups at eight weeks. These results indicate that *B. pasteurii* and *L. sporogenes* administered orally as dietary supplements metabolize urea and creatine in vitro in subjects. Whether similar activity is discerned in uremic patients and large animals is the subject of derivative study. *L. acidophilus* (NCFM) fed dialysis patients reduced uremic toxins and showed improved nutritional status of about a ten percent increase in daily caloric intake and 1.6% increase in BMI (p<0.05) with no side effects. This study used a rat model of CRF (⅚ nephrectomy) to test 6 non-pathogenic microorganisms (MO) for possible use in a probiotic product. Sixty rats had ⅚ nephrectomies performed. Baseline creatine levels(Scr), BUN were measured and Cr clearance calculated. Rats (18 male and 18 female) with sufficient renal impairment (Scr=1.0=/−0.4) were distributed into 6 matched groups (GP), ANOVA showed no significant difference between groups (p=0.516) at baseline. Rats were individually caged and fed a special diet beginning at day 30 supplemented with a particular MO additive daily for up to 126 days. Periodic BW, Scr, BUN and CrCl were measured. A control group of non-nephrectomized rats(n=7, Scr=0.2+/−0.1) received the same food without any supplement. All of the rats survived (Scr at end=0.5=/−0.1). Days of survival was the primary endpoint variable. The study ended at day 156.

TABLE 1

Survival in Groups of Mice Receiving Oral Diet Supplements Containing Non-Pathogenic Microorganism

| GP | Organism | ALIVE | DEAD | % SURVIVE | Mean days | SD | Median |
|---|---|---|---|---|---|---|---|
| G | *S. boulardi* | 2 | 4 | 33.3 | 111 | 44 | 113 |
| B | Placebo | 2 | 4 | 33.3 | 116 | 39 | 122 |
| F | H1001 | 2 | 4 | 33.3 | 116 | 36 | 110 |
| E | SF101 | 3 | 3 | 50 | 126 | 33 | 132 |
| C | *B. pasteruii* | 4 | 2 | 66.7 | 148 | 14 | 156 |
| D | *L. sporogenes* | 5 | 1 | 83.3 | 149 | 16 | 156 |

As shown in Table 1, diets D and C were more effective than G, B, and F (p<0.05). The study showed that a probiotic containing either or both *B. pasteurii* and *L. sporogenes* is capable of increasing survival in otherwise untreated uremic rats.

In another aspect, the present invention further provides compositions for treating uremia or renal dysfunction in a subject, comprising a mixture of one or more selected bacteria which converts nitrogenous waste into non-toxic compounds in vivo along with one or more of the following: a prebiotic, ammoniaphilic bacteria with high urease activity, and/or sorbents with specific adsorption affinities for uremic toxins such as creatinine, uric acid, phenols, indoles, middle molecular weight molecules and inorganic phosphate along with a water sorbent, for use in the alleviation of uremia.

Compositions comprising selected bacteria which converts nitrogenous waste into non-toxic compounds in vivo may be enteric coated and/or microencapsulated. Enteric coating of the composition is specifically designed to deliver sorbents and/or the selected bacterial source at the ileal and colonic regions of the bowel where maximal resorption of uremic solutes and other molecules are found to occur. This is preferably achieved via a coating material that disintegrates and dissolves at a pH of 7.5 or higher. Examples of enteric coatings with these characteristics include, but are not limited to, Zein, polyglycolactic acid, polylactic acid, polylactide-co-glycolide and similar coating materials. Enteric coatings also enable delivery of the sorbents to their site of action in relatively native form without binding of various digestive materials to the sorbents prior to reaching the target region.

Compositions of the present invention may further comprise a phosphate binding agent such as aluminum hydroxide gel, calcium carbonate or calcium acetate, magnesium hydroxide gel and/or a water binding agent such as psyllium fibers, naturally occurring gums such as locust bean gum, guar gum or modified starches.

Compositions of the present invention are administered orally to subjects in need thereof to decrease the build-up of toxins and metabolic wastes and/or to inhibit or decrease the over growth of undesirable bacteria in the subject. In one embodiment, the composition is administered to a subject with uremia to alleviate the symptoms of uremia. By "alleviation of symptoms" of uremia, it is meant that the composition removes sufficient levels of uremic toxins such that a patient suffering from uremia either does not require dialysis, requires dialysis less frequently or for shorter durations, or does not require initiation of dialysis as soon as would be needed without treatment. Compositions of the present invention can also be administered to a subject in need thereof to treat not only renal insufficiency and inborn error of urea metabolism, but also liver insufficiency and gastrointestinal disorders and diseases.

In a preferred embodiment, oral delivery of the compositions is accomplished via an emulsion or paste mixed with an easy to eat food. The oral delivery of the compositions may be via ready to eat food or other nutritional product. The delivery of the compositions of the present invention may be via pharmaceutical compositions of liquid, capsule, pill or other suitable forms. The probiotic or selected bacteria of this invention can be administered along with a mixture of sorbents in the emulsion or paste or separately in an ingestible capsule.

What is claimed is:

1. A composition for treatment of renal failure comprising *Bacillus pasteurii* which converts nitrogenous waste into non-toxic compounds in vivo, wherein said *Bacillus pasteurii* is enterically coated.

* * * * *